(12) United States Patent
Spartz

(10) Patent No.: US 11,977,024 B2
(45) Date of Patent: May 7, 2024

(54) METHOD AND SYSTEM FOR LOW DETECTION LIMIT EO USING PRESSURE, CHILLER AND REACTOR

(71) Applicant: MLS ACQ, Inc., East Windsor, CT (US)

(72) Inventor: Martin L. Spartz, Ellington, CT (US)

(73) Assignee: MLS ACQ, Inc., East Windsor, CO (US)

( * ) Notice: Subject to any disclaimer, the term of this patent is extended or adjusted under 35 U.S.C. 154(b) by 112 days.

(21) Appl. No.: 17/644,504

(22) Filed: Dec. 15, 2021

(65) Prior Publication Data

US 2022/0187201 A1 Jun. 16, 2022

Related U.S. Application Data

(60) Provisional application No. 63/126,250, filed on Dec. 16, 2020.

(51) Int. Cl.
| | | |
|---|---|---|
| *G01N 33/68* | (2006.01) | |
| *A01N 1/02* | (2006.01) | |
| *B01J 19/00* | (2006.01) | |
| *B01J 23/42* | (2006.01) | |
| *B01L 3/00* | (2006.01) | |
| *C07C 309/65* | (2006.01) | |
| *C07C 309/73* | (2006.01) | |
| *G01N 1/40* | (2006.01) | |
| *G01N 21/01* | (2006.01) | |
| *G01N 21/31* | (2006.01) | |
| *G01N 21/33* | (2006.01) | |
| *G01N 21/35* | (2014.01) | |
| *G01N 21/3504* | (2014.01) | |

(Continued)

(52) U.S. Cl.
CPC ...... *G01N 21/3504* (2013.01); *B01J 19/0013* (2013.01); *B01J 23/42* (2013.01); *G01N 2021/3595* (2013.01)

(58) Field of Classification Search
CPC ....... G01N 21/3504; G01N 2021/3595; G01N 33/0026; G01N 2021/399; B01J 19/0013; B01J 23/42; B01J 19/0073; B01J 2208/0053; B01J 2208/00628; B01J 2219/00011; B01J 2219/00159; B01J 2219/00957; B01J 19/0093; B01J 19/12; B01J 19/0006
See application file for complete search history.

(56) References Cited

U.S. PATENT DOCUMENTS

| | | | | |
|---|---|---|---|---|
| 2,976,414 A | * | 3/1961 | Heinz | ............... G01N 21/3504 250/341.1 |
| 9,606,088 B2 | | 3/2017 | Spartz et al. | |

(Continued)

FOREIGN PATENT DOCUMENTS

WO WO-2017177154 A1 * 10/2017 ......... G01N 21/3504

OTHER PUBLICATIONS

United States Patent Office Action for U.S. Appl. No. 17/119,297 dated May 26, 2023 (9 pages).

(Continued)

*Primary Examiner* — Jennifer Wecker
*Assistant Examiner* — Oyeleye Alexander Alabi
(74) *Attorney, Agent, or Firm* — Michael Best & Friedrich LLP

(57) ABSTRACT

A gas analysis system and method using a spectrometer, such as a Fourier transform infrared spectrometer, utilizes a reactor, such as a catalytic reactor, for providing interference spectra. The gas is pressurized and chilled to remove water prior to the spectrometer.

21 Claims, 5 Drawing Sheets

(51) Int. Cl.
  *G01N 21/64*    (2006.01)
  *G01N 27/414*   (2006.01)
  *G01N 33/52*    (2006.01)
  *G01N 33/532*   (2006.01)
  *G01N 33/543*   (2006.01)
  *G01N 33/569*   (2006.01)
  *G01N 33/72*    (2006.01)
  *G01N 35/00*    (2006.01)
  *G01N 35/02*    (2006.01)
  *G01N 35/04*    (2006.01)
  *G01N 35/10*    (2006.01)

(56) References Cited

U.S. PATENT DOCUMENTS

| | | | |
|---|---|---|---|
| 10,054,486 B2 | 7/2018 | Spartz et al. | |
| 10,295,517 B2 | 5/2019 | Birks et al. | |
| 10,408,746 B2 | 9/2019 | Spartz et al. | |
| 11,187,585 B2 | 11/2021 | Spartz | |
| 2008/0180661 A1* | 7/2008 | Brown | G01N 21/65 |
| | | | 356/301 |
| 2015/0260695 A1 | 9/2015 | Spartz | |
| 2017/0341056 A1* | 11/2017 | Spartz | G01N 30/88 |
| 2018/0252639 A1* | 9/2018 | Spartz | G01N 21/643 |
| 2020/0116569 A1 | 4/2020 | Spartz | |
| 2021/0178352 A1 | 6/2021 | Spartz | |

OTHER PUBLICATIONS

Model 49i; Instruction Manual; UV Photometric 03 Analyzer Part No. 102434-00; Sep. 25, 2017.

Thermoscientific, "Model 49i Instruction Manual, UV Photometric O3 Analyzer Part No. 102434-00", Sep. 25, 2017, 314 pages.

* cited by examiner

METHOD AND SYSTEM FOR LOW DETECTION LIMIT EO USING PRESSURE, CHILLER AND REACTOR

RELATED APPLICATIONS

This application claims the benefit under 35 USC 119(e) of U.S. Provisional Application No. 63/126,250, filed on Dec. 16, 2020, which is incorporated herein by reference in its entirety.

BACKGROUND OF THE INVENTION

U.S. patent application Ser. No. 16/653,689, filed on Oct. 15, 2019, by Spartz, now U.S. Pat. Pub. No. US 2020/0116569 A1, now U.S. Pat. No. 11,187,585, entitled "FTIR Spectrometer with Optical Filter for Low Level Gas Detection such as Formaldehyde and Ethylene Oxide"; U.S. patent application Ser. No. 14/660,574, filed on Mar. 17, 2015, now U.S. Pat. Pub. No. US 2015/0260695 A1, now U.S. Pat. No. 9,606,088, entitled "Process and System for Rapid Sample Analysis"; and U.S. patent application Ser. No. 15/433,016, filed on Feb. 15, 2017, now U.S. Pat. Pub. No. US 2017-0160136, now U.S. Pat. No. 10,054,486, entitled "Process and System for Sample Analysis"; all these documents being incorporated herein by this reference (hereinafter Spartz patent), describes a Fourier transform infrared (FTIR) spectrometer for low level gas detection of chemicals such as Formaldehyde and Ethylene Oxide. In particular, it discloses FTIR spectrometers employing optical filters in their interferometers for improving performance by generating bandlimited interferograms.

Nevertheless, spectral interferences can still be an issue for very low detection levels. Generally, infrared measurements are managed by having a precise library of pure component calibration spectra. The best matches normally achieved between a library calibration spectrum of a given pure component and a sample spectrum of that pure component are only about 1% of the intensity, however. The difference between the sample spectrum and the calibration spectrum is called the residual spectrum. In most cases, the residual spectrum is about 1 to 2% of the sample intensity. If an interference feature has an absorption of 0.10 abs, the best residual achievable would be ~0.001 abs. On the other hand, if the calibration spectrum is collected by the same instrument, the best matches can be 0.1% or ~0.0001 abs. Even this is not good enough if the analyte of interest is 100's, 1,000's, 10,000's, or 100,000's times smaller than the interfering sample matrix, however.

In the past, ultraviolet (UV) oxidation has been used to remove or convert an analyte to another compound to make it possible to measure. In one case, a cell called PAPA was developed. PAPA stands for Photo Assisted Pollution Analysis. See also U.S. Pat. No. 10,408,746 in which a furnace is used to convert reduced sulfur present in food-grade carbon dioxide to sulfur dioxide so that it can be better detected by an FTIR.

SUMMARY OF THE INVENTION

When attempting to measure compounds with features many orders of magnitude lower than one or more an interfering specie, a better spectral interference method is required for accurate analysis to limit biases from those interferences. The best spectral match achievable on any absorption-based spectrometer is an interference spectrum that is measured on the same instrument, at the same concentration, and in a similar, recent time frame (potentially same day, week or month).

Consider the problem of measuring ethylene oxide (EO) at single digit parts per billion (ppb) levels for continuous process abatement exhaust (CEM) and at parts-per-trillion (ppt) levels for ambient air monitoring. 1 ppb of ethylene oxide at 1 atmosphere (atm) pressure, at 150° C. and collected at 2×8 $cm^{-1}$ resolution in a 5.11 meter gas cell only has an infrared absorption feature of 2.5 µAbs units; this represents 16,000 times less than a 2% water (common in air) absorption feature or 0.04 Abs in that region.

In general, some of the objectives of the invention include one or more of the following: to reduce interferences such as by reducing water in the sample, to develop a procedure and/or technology to determine the exact interference spectra of the current or near current sample, without the necessity of collection of new pure component calibration spectra; to implement a process for removing the analyte(s) of interest from the sample stream, without changing the sample matrix, preferably using a simple procedure or one that could be automated by a continuous monitoring system for process, environmental or IH (industrial hygiene—ambient air); to produce a switched reaction device that could be attached to any spectrometric system to allow for the switching of the sample (analyte+matrix) stream to a sample matrix only stream. In practice, the interference spectrum would be included in the automated analysis, and/or could be used as the interference spectrum for future sample spectra.

These techniques are also applicable as a zero mechanism for measuring Chemical Warfare agents. If those agents are reactive, a method to zero a chemical agent detection system is practical.

In addition, techniques described herein can be used to remove an interference if the interferents were more reactive than the analyte of interest and then perform a direct measurement of the analyte without the interference. One example is measuring siloxanes in the presence of numerous oxygenated hydrocarbons present in biogas, where the oxygenated hydrocarbons are removed to perform a direct siloxane measurement.

In more detail, one approach to temporarily remove an analyte of interest such as EO to obtain requisite interference spectra involves flowing the sample stream through a reactor, such as a heated oxidation catalyst, a hot furnace reactor, UV illumination or photo-ionization, chemical reaction with reagent or other of a switched reaction device. Details of construction and design include a reaction chamber that holds an oxidation catalyst (different catalysts could be used depending on the compound of interest, such as sulfur compounds) or a furnace reactor. In the oxidation catalyst configuration, a heated sample line is ideally incorporated to raise the gas temperature to the catalyst temperature before reaching the catalytic reactor to ensure full removal of the analyte. This heated line can be part of the heated oxidation catalyst reactor for design efficiency. An automated valve system is included to switch between sample (analyte+ sample matrix) and sample matrix only. The analysis software executing on the spectrometer controller is used to collect both the sample spectra and interference spectra. The system can then utilize the interference spectra in analyzing the sample. Additionally, the spectrometer controller could also determine when to switch from sample measurement mode to interference measurement mode, most likely by monitoring the magnitude of the residual spectrum between the interference spectra and the sample spectra. The reactor is connected to a sampling system that pulls or pushes the sample through the reactor and then onto the FTIR or other analyzer.

To further improve performance, the water in the sample stream is reduced and preferably reduced to a known level. In most applications, water tends to be the largest spectral interference when monitoring for EQ. Also, it can be present at widely different levels, depending on sample type, application (e.g., Ambient Air (cold weather/warm weather), Process Streams (hot and cold), Environmental Abatement systems (hot and cold) or other factors. Typically, the warmer the stream the greater the potential for water to be at higher and often widely fluctuating concentrations. Neither of those situations is ideal for low-level EO monitoring by FTIR or other optical techniques (cavity ring down, laser, etc) in the infrared region since the water absorption features can be 1,000s of times higher than that of a typical analyte such as EQ.

In one implementation, a pressurization pump is added to pressurize the incoming sample stream. Then, the pressurized stream is passed through a chiller to cool the stream and condense the water to the vapor pressure of the chiller. The pressure can then be reduced (to reduce the water further by the ratio of the two pressures), or not, prior to a switched reaction device for selectively providing a sample stream or a reacted sample stream to the spectrometer, and a controller using the reacted sample stream to create interference spectra for analyzing the sample stream.

In different embodiments, the spectrometer analyzes the gas at negative or positive atmospheric pressures. Analysis at atmospheric pressure also is possible.

In one implementation, the switched reaction device simultaneously flows one of the sample streams and the reacted sample stream to the spectrometer, while the other one is directed to an exhaust. In other cases the two streams (namely the sample stream and the reacted sample stream) are switched on and off, in an alternating fashion.

Preferably, the reaction device comprises a preheater for heating the sample stream before it is flown into the reactor.

Different reactors can be used such as a thermal catalytic oxidizer reactor, furnace reactor, UV illumination or photo-ionization reactor, or chemical reactor with reagent to remove interference gas(es) and/or analyte(s).

Different spectrometers can be used such as infrared absorption spectrometers, mass spectrometers, cavity ring down spectrometers, ion mobility spectrometers, electrochemical sensors, or gas chromatographs.

In general, according to one aspect, the invention features a gas analysis system comprising: a spectrometer for analyzing gas, a reaction device for selectively providing a sample stream or a reacted sample stream to the spectrometer, and a controller using the reacted sample stream to create spectra for analyzing the sample stream.

Preferably a system for reducing water in the gas upstream of the reaction device is used. Such system might include a pressurization pump to pressurize the incoming gas and possibly a chiller to cool pressurized gas.

In different use-cases, the controller analyzes the spectra for measuring ethylene oxide and/or siloxanes.

The reaction device can take a number of forms and can include an oxidation catalyst and/or a furnace reactor.

In operation, the controller might determine when to switch from sample measurement mode, using the sample stream, to interference measurement mode, using the reacted sample stream.

The control can determine when to switch from the sample measurement mode to the interference measurement mode by monitoring a residual spectrum.

The reaction device can include a preheater for heating before flowing into a reactor.

The reaction device can include a thermal catalytic oxidizer reactor, UV illumination or photo-ionization reactor, or chemical reactor with reagent to remove interference gas(es) and/or analyte(s).

The spectrometer can include infrared absorption spectrometers, e.g., Fourier transform spectrometer, mass spectrometers, ion mobility spectrometers, cavity ring down spectrometer, electrochemical sensors, or gas chromatographs.

In general, according to another aspect, the invention features a gas analysis method, comprising analyzing gas with a spectrometer, switching/alternating between a sample mode and an interference mode for selectively providing a sample stream or a reacted sample stream to the spectrometer; and using the reacted sample stream to create spectra for analyzing the sample stream.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Ethylene oxide (EO) is an extremely reactive material that is widely used in the chemical industry as a precursor for many polymeric and chemical processes. Since the two main EO infrared interferences are water and methane, it is possible that its reactivity could be used to remove it from the sample stream and measure the infrared interference spectrum of the sample matrix (i.e., a stream containing all components present in the sample except for the analyte of interest) extremely accurately. Then, those accurate interference spectra could be added to the analysis method to predict the EO present in the unreacted, sample stream.

Figure 1:
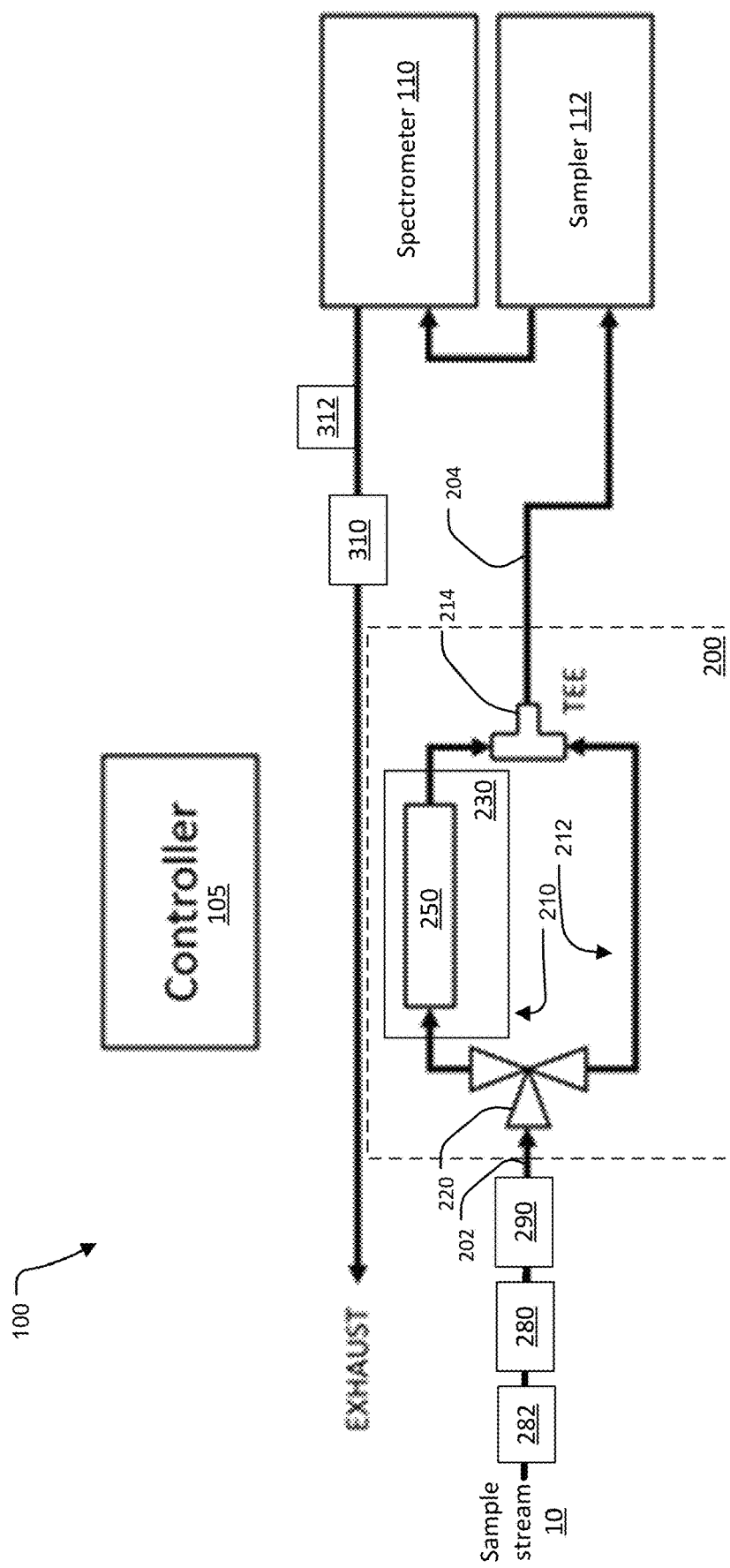
FIG. 1 is a schematic diagram of a gas analysis system of the present invention.

FIG. 1 shows a gas analysis system 100 that has been constructed according to the principles of the present invention.

The system 100 is controlled by a controller 105. A spectrometer 110 detects spectra of gases contained in its sample (also referred to herein as a 'gas") cell, for example, and reports those spectra to the controller 105.

In the current embodiment, the spectrometer 110 is an infrared absorption spectrometer, and particularly a FTIR spectrometer. However, in other embodiments, different infrared absorption spectrometers could be used including dispersive spectrometers and non-dispersive spectrometers such as tunable diode laser absorption spectrometers (TD-LAS), cavity ringdown spectrometers (CRDS) as well as UV and VUV absorption spectrometers.

In addition, spectrometers other than absorption spectrometers could be used, such as mass spectrometers, ion mobility spectrometers, electrochemical sensors and potentially gas chromatographs.

The gas input to the spectrometer 110 is provided by a sampler 112. In this configuration, the sampler includes a sampling pump that pulls the gas from the sample (ambient air or process). The gas, optionally filtered for particulate matter, is pushed onto the spectrometer.

In specific implementations, the sample gas stream directed to the sampler 112 is preprocessed through a number of stages.

First, the sample stream 10 is pressurized by a pressurizing system 282 such as a pump, e.g., a piston pump or another suitable device. The operation can increase the pressure of the sample stream by at least a factor of two. In some examples, the pressure is increased to over 3 atmospheres (atm), such as 5 atm or more, or as high as 10 atm, or more.

A chiller system 280 accepts the pressurized gas of the sample stream from the pressurizing system 282 and cools the pressurized sample stream gas, condensing the moisture from the sample. The condensate is then expunged, e.g., through a drain orifice valve on the bottom of the chiller.

In some examples, the chiller system 280 cools the pressurized gas to less than 10° C., such as about 4° C., since the exiting gas (from the chiller system) can only contain about 6.1 Torr of water partial pressure at 4° C. at any pressure. As the total pressure increases the water exiting quickly reaches an equilibrium of about 6.1 Torr and can go no higher unless the temperature of the chiller is raised.

In one example, the chiller system 280 is a two staged chiller, such as a Peltier chiller maintained at ~4 C that uses impinger type chambers to capture the condensing water.

The bottom of each impinger can be provided with a drain that would connect to a small valve to push out the condensed water by the pressurized gas.

From the chiller system 280, the sample then passes through a mass flow controller (MFC) or a controlled orifice 290 to set the output flow rate and to drop the pressure to ambient atmospheric pressure (1 atm) or to some other pressure level that is lower than the chiller pressure, such as less than 3 atm or 2 atm.

In modes in which the sample in the gas cell of the spectrometer 110 is pressurized to greater than 1 atm such as greater than 2 atm or greater than 3 atm, a back pressure regulator 310 is added downstream of the gas cell, and upstream of the exhaust to maintain the desired pressure in the gas cell. Preferably the back pressure regulators 310 is feedback controlled by the controller 105 based on a pressure signal from a pressure transducer 312 that senses the pressure in the gas cell.

This approach has been tested with the prototype chiller system. The partial pressure of the moisture exiting the system was measured in the 6 Torr range and was found to be fairly constant, when the sample exited at 5 atm. With a constant moisture level, the system should be able to run for longer periods before having to collect a new interference spectrum, as described below.

By operating in this manner, the characteristics of the sample stream are no longer as important since the absolute moisture level is determined by the temperature of the chiller and the relative moisture level is determined by both the chiller and the sample pressure in the chiller.

A switched reaction device 200, under control of the controller 105, provides the gas interface between the sample stream 10 and the sampler 112.

The switched reaction device 200 receives the sample stream gas on an input line 202 and supplies gas to the sampler 112 on an output line 204. The switched reaction device 200 includes a reactor path 210 that passes the sample stream gas through a reactor 250 and a bypass path 212 that avoids the reactor 250.

There are a number of ways of implementing the reactor 250. In one example, the reactor is a heated oxidation catalytic reactor. In another example, the reactor is a hot furnace reactor. In still other examples, the reactor is a UV illumination reactor, photo-ionization reactor, or chemical reactor with reagent. Selecting the appropriate type of reactor may depend on the nature of the analyte to be removed, convenience, available technologies and/or other factors. In one example, an analyte is converted by conducting a chemical reaction of one or more other compounds, generating a reaction product that does not present spectral features in the wavelength region of interest, allowing measurements of the sample matrix.

The present oxidative approach employs a switched reaction device 200 with a small catalytic reactor with one or more oxidation catalysts. The switched reaction device 200 includes a heater system 230 that is controlled by the system controller 105 to raise the temperature of the reactor to the point where EO is consumed but the water and methane (as well as other potential organic material) of the sample matrix pass through unchanged.

System 100 further includes an automated valve system 220 that controls (through controller 105, for instance) whether gas from the reactor path 210 or from the bypass path 212 is provided to the sampler 112 and then to the spectrometer 110.

In the illustrated example, the automated valve system 220 is on the upstream side of the switched reaction device 200 with a T-junction 214 on the downstream side. Other configurations are possible, however. For example, the sample stream could flow continuously through both the reactor path 210 and the bypass path 212. Then the automated valve system 220 would simply divert the output of one of these paths onto the spectrometer 110. In another example, the automated valve system 220 is on the downstream side of the switched reaction device 200 with a T-junction on the upstream side.

In the case of detecting low-level EO using a FTIR spectrometer, the spectrometer 110 is preferably configured as described in the Spartz patent. To summarize, it uses a narrow band detector of HgCdTe (MCT) or InAs, e.g., a 4 or 5-μm cutoff, that has much higher Detectivity "D*" than standard MCT detectors. D* is the photo sensitivity per unit active area of the detector. In the current embodiment, peak detectivity "D*" of the detector is preferably higher than $1\times10^{10}$. Preferably, it is about $1\times10^{11}$. This higher D* provides the framework to obtain much higher signal-to-noise spectral data and produce much lower detection limits for compounds with spectral features in the 1 to 5 μm spectral region. An optical filter with a band pass of less than 450 $cm^{-1}$ filters the light received by the FTIR's detector. Typically the filter band pass is smaller, such as less than 300 $cm^{-1}$, e.g., about 150 $cm^{-1}$ in some cases. Preferably, the filter is placed in front of the detector. Typically, the center wavelength of the filter's band pass is between 3 and 4 μm.

The sample stream from the bypass path 212 and reactor stream from the reactor path 210 are configured in parallel paths both leading to the spectrometer 110, such as the FTIR spectrometer described above. In operation, the input to the FTIR analyzer gas cell is switched back and forth between the sample stream and reactor stream by the controller's operation of the valve system 220, as needed to collect the absorption spectra of the sample and the absorption (interference) spectra of the sample matrix, also referred to herein as the reacted sample stream.

In one mode of operation, controller 105 is configured to automatically trigger the switch to the reactor stream when the EO residual error reaches a critical point, such as by control of automated valve system 220.

From previous research it is known that higher molecular weight organic materials oxidize when passed across an oxidation catalyst at temperatures of only 200° C. Due to EO's reactivity, it can be fully removed by a dual oxidation catalyst at temperatures below 125° C. Thus, a very inexpensive catalytic reactor can be built with routine materials and without the need for a high temperature furnace.

In the illustrated embodiment the sampler 112, typically a pump, is located downstream of the switched reaction device 200, but in general the sampling pump can be before or after the reaction device.

From experimentation, it appears that another optimal configuration would have the incoming sample gas evenly split with half flowing continuously through the bypass channel (path 212) while the other half is constantly flowing through the reactor channel (reactor path 210). A selector valve is then utilized to select the gas stream that is directed to the gas analyzer (spectrometer 110, for example) in order to provide the operation of the switched reaction device 200.

However, if both channels are flowing continuously, it is ideal to have the sample pump 112 before the reaction device 200 so that constant flows may be maintained for both sample paths. Additionally, higher pressures can be utilized if the sample pump 112 is positioned before the reaction device 200. Up to 60 psig reactor pressures and a 5 liters per min flow have been demonstrated with excellent EO removal in the oxidizer mode. It has been shown that having both paths (reactor path 210 and the bypass path 212) flow simultaneously, there is a much lower change in the moisture level between the two paths. In general, since an important objective is water interference elimination, water should thus be kept constant on both paths.

The system can be operated in different modes. In one example, the pressure is lowered after the chiller 280 but before the reaction device 200 by a valve on input line 202. In this way, the pressure can be released once the moisture is removed and measurements can then be made at a lower but above atmospheric or at atmospheric pressure.

In one example, if the sample gas is pressurized to 10 atm in the chiller and is operated at 4° C., the sample exiting the chiller would contain ~6.1 Torr of water. If the pressure is then reduced to 1 atm for measurement, the moisture would drop to ~0.61 Torr within that 1 atm stream. Advantageously, the moisture variability drops as well in the exiting gas stream.

Without pressurization, to reach this lower partial pressure of moisture (or ~0.61 Torr), the chiller would have to operate at −22.5 C. At this temperature, the water would freeze (causing issues) and the EO would potentially condense and become captured within the frozen ice. This is not ideal if a quantitative measurement of the EO is required.

Figure 2A:
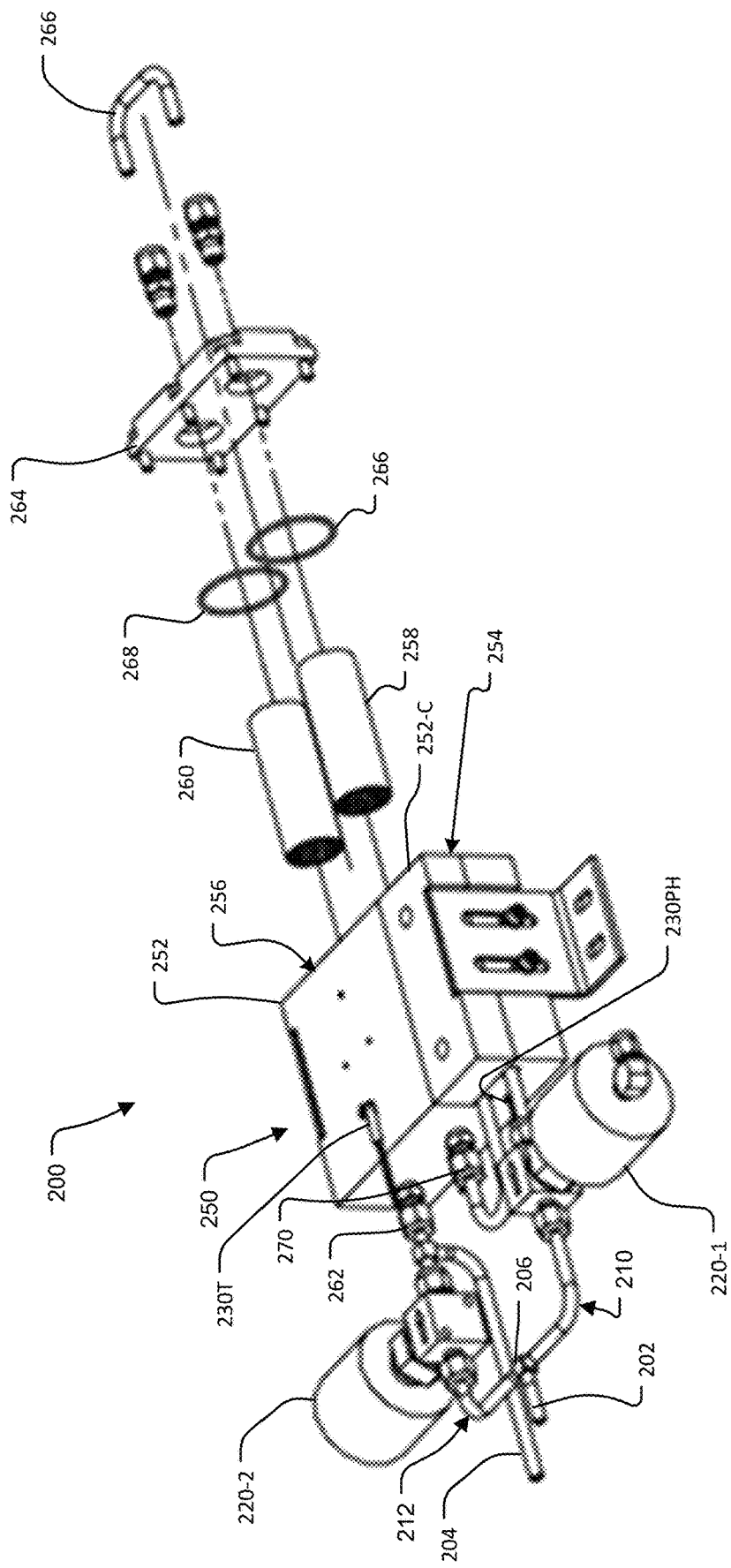
FIGS. 2A and 2B are exploded perspective scale views of a switched reaction device of the invention.
Figure 2B:
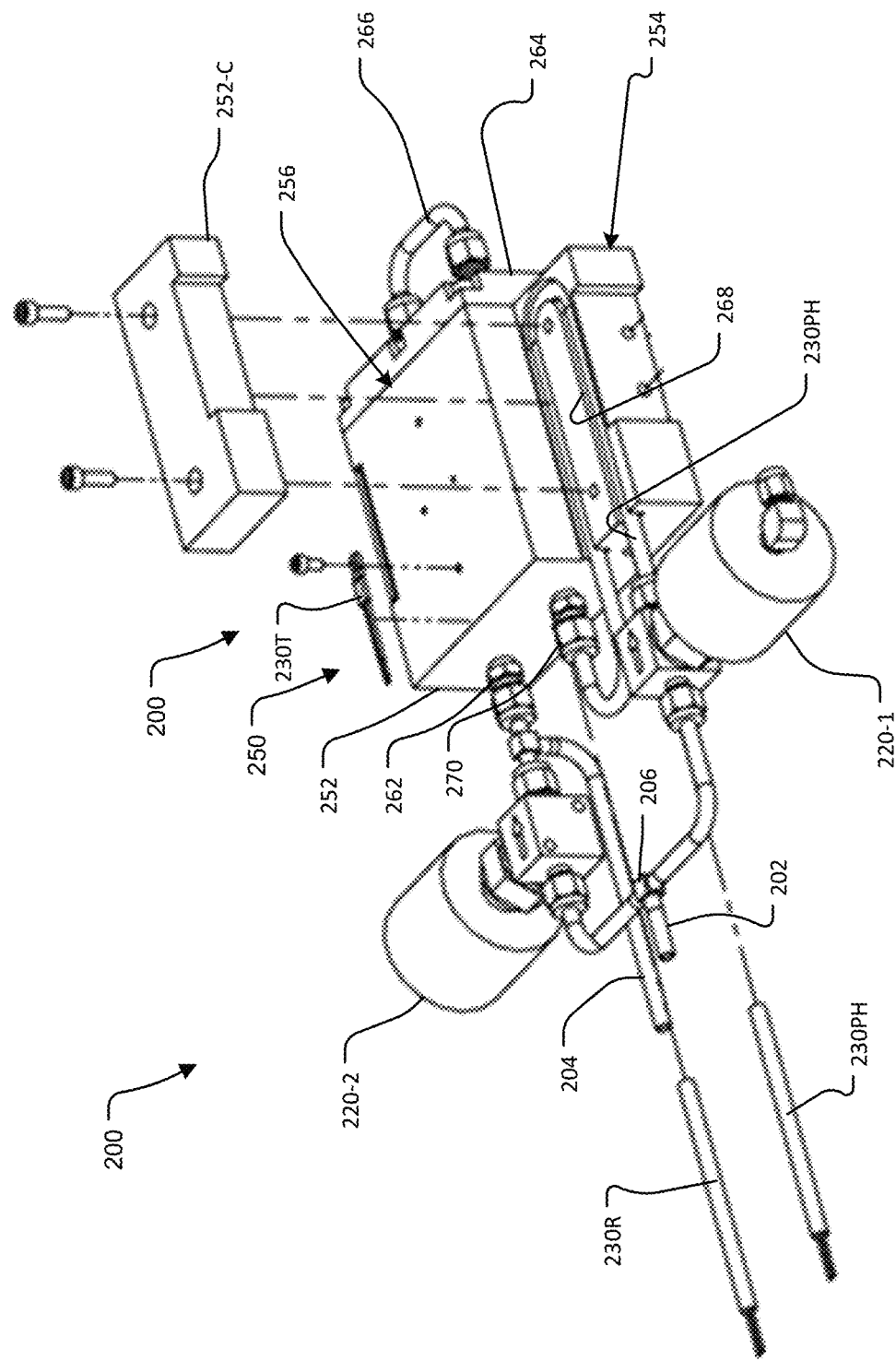

FIGS. 2A and 2B are exploded views of the switched reaction device 200.

The sample stream 10 is received on the input line 202. It is coupled to T-section 206 that divides the sample stream between the reactor path 210 and the bypass path 212.

On the bypass path 212, a bypass valve 220-2 of the automated valve system 220 is operated by the system controller 105 to couple the sample stream to the output line 204.

On the reactor path 210, a reactor valve 220-1 is also operated by the system controller 105 to couple the sample stream into the reactor 250.

The valves 220-1, 220-2 in the current design are pneumatically actuated to allow them to operate properly at higher temperatures. An 80 psig ($N_2$ or CDA—Clean Dry Air) stream is utilized to actuate the valves and is controlled by a single stage pressure regulator that is controlled by the controller 105.

The reactor 250 comprises a housing 252 that includes a preheater section 254 for preheating the incoming sample stream. A subsequent catalyst section 256 receives the preheated sample gas from the preheater section 254 and directs the gas through two serial catalyst cores 258, 260, inserted within the housing 252. A U-shaped tubing section 266 couples the gas from the first core 258 to the second core 260. Finally, the gas leaves the reactor 250 via reactor output line 262, which is coupled to device output line 204.

The housing 252 is constructed from an aluminum block with two reaction chamber holes drilled into the distal side of the housing 252 to accommodate the 1×3.5-inch cylindrical catalyst cores 258, 260. The housing has a removable preheater cap 252-C that is bolted to the body of the housing 252. Removal of the cap 252-C exposes the preheater tubing 268 extending through a path formed in the housing. Other configurations and/or materials can be employed.

Ideal catalysts are those platinum catalysts commonly used to remove organic material like formaldehyde emanating from natural gas fired rotary internal combustion engines (RICE).

A sealing plate 264 is bolted to the distal side of the housing 252 sealing the mouths of the first and second reaction chamber holes. Appropriately sized o-rings 266, 268 prevent the sample stream from flowing around the catalyst cores 258, 260 as it passes through the two reaction chambers.

In the illustrated embodiment, the heater system 230 includes a preheater cartridge heater 230PH, a reactor cartridge heater, and a temperature sensor thermocouple 230T. In FIG. 2A, the preheater cartridge heater 230PH and reactor cartridge heater are shown inserted into holes formed in the bulk of the housing 252; and FIG. 2B shows them exploded from those holes. The temperature sensor thermocouple 230T is bonded to a top face of the housing 252. Note that the reactor cartridge heater and its insertion hole in the housing 252 are obscured by coupling 270 in the view of FIG. 2A.

Generally, the controller 105 powers the preheater cartridge heater 230PH and reactor cartridge heater 230R in order to maintain the housing at the desired temperature, e.g., greater than 100° C. and preferably greater than 110° C., such as 125° C. for EO oxidation and removal. The controller 105 monitors the thermocouple 230T in order to provide stable, feedback controlled, temperatures.

Figure 3:
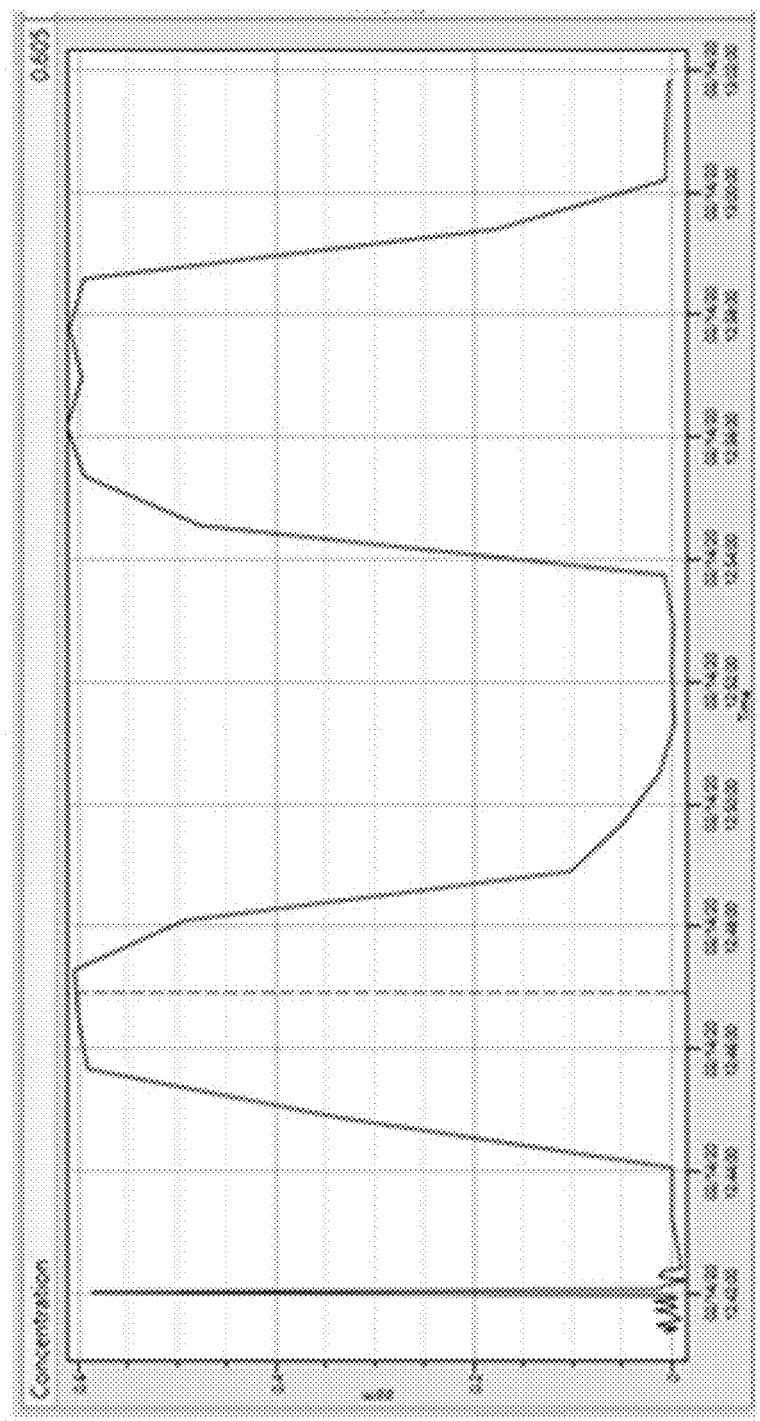
FIG. 3 is a plot of concentration detected showing the operation of the reactor.

FIG. 3 is a plot of concentration detected by the spectrometer 110 and presented by the controller 105 over time. Here, a continuous flow of 600 ppb EO was provided in the sample stream 10. The peaks and troughs are associated with the controller 105 switching between the reactor path 210 and the bypass path 212, respectively. At the beginning of the trace the sample gas is passed through the reactor (oxidizer mode) to oxidize all the EO, then the gas stream is switched to bypass to measure the EO; it is then switched between reactor and bypass another time to demonstrate the ability of the reaction device 200 to remove the EO from the sample stream.

The removal of the EO from a sample stream allows the controller 105 to create an interference spectrum for the sample matrix near-identical to the sample stream for usage in the regression algorithm.

Both water and methane are present in ambient air and both interfere spectrally in the infrared spectral region with EO. As a result, having two interference spectra (along with the EO calibration spectra) with varying amounts of each interferent can help improve the EO analysis (i.e., 2 equations—2 unknowns).

This component removal concept could be utilized for nearly any analyte (e.g., hazardous air pollutants (HAPs), like Benzene, Toluene Xylenes in ambient air) where the interferents (water, methane and carbon dioxide) are less reactive than the analyte of interest and the resultant sample gas is measured through an optical technique.

Other methodologies can be employed by the reactor device 200. Besides a catalytic oxidizer, such as a furnace operating at high temperature, device 200 can employ a UV source or an additional reaction gas to remove the analyte of interest.

The reactor device 200 employing a thermal oxidizer or furnace reactor could also be used to remove interference species that are more reactive than the analyte(s) of interest such that the analyte can be measured directly without the presence of the interference. An example of this application would be the removal of oxygenated hydrocarbons in biogas to measure siloxane contamination. In most biogas streams there are high levels of oxygenated hydrocarbons that spectrally overlap with the strongest siloxane absorption bands making their quantification difficult. If these oxygenated hydrocarbon gases were removed, e.g., according to principles described herein, direct spectroscopic measurements would become feasible, without the need for separation techniques such as gas chromatography.

Figure 4:
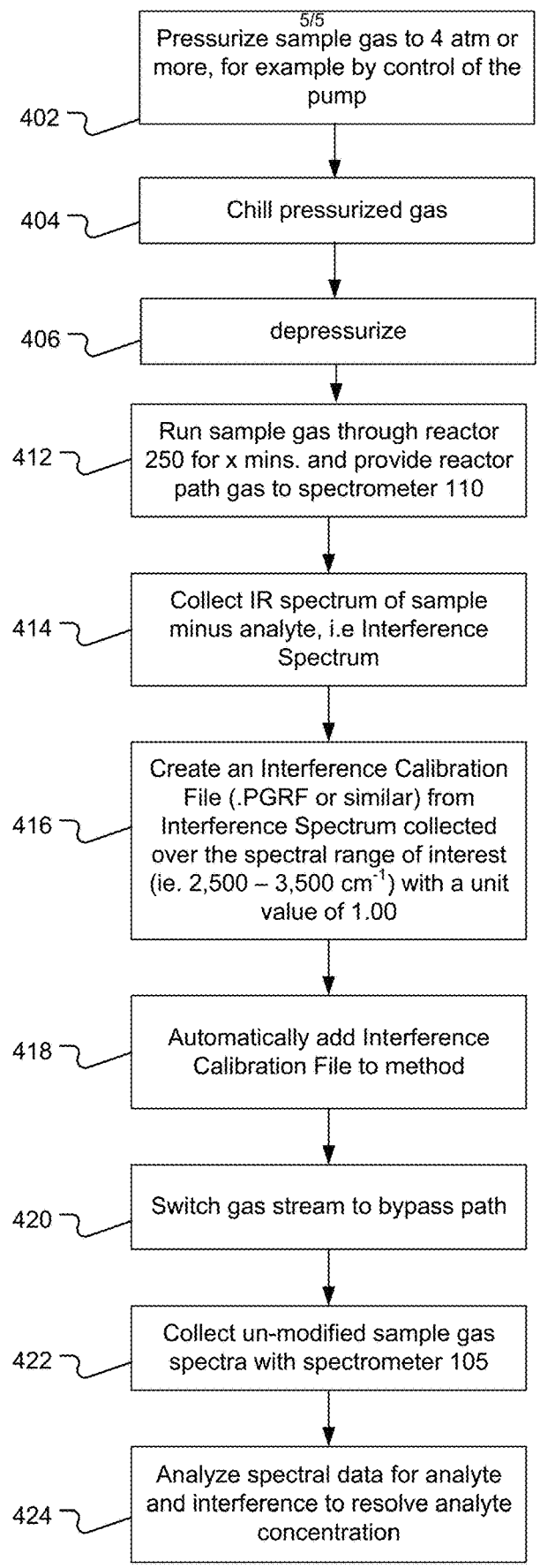
FIG. 4 is a flow diagram showing the operations performed by the controller and the control of the gas analysis system for a basic interference spectrum collection and analysis.

FIG. 4 is a flow diagram showing the operations performed by the controller 105 and the control of the gas analysis system 100 for a basic interference spectrum collection and analysis.

In step 402, the gas stream 10 is pressurized by the pressurizing system 282. In specific implementations, the system includes a pressure transducer to allow feedback control by the controller 105 to the desired pressure.

In step 404, the pressurized gas stream is cooled in the chiller 280 to remove moisture, while in step 406, the MFC 290 (under the control of controller 105) controls the flow and pressure into the reactor 250.

In step 412, the sample gas from the MFC is directed through the reactor 250 for a specified period of time. Typically, this operation takes at least one minute and often several minutes. This is effected by the controller 105 controlling the automated valve system 222 to direct the gas through the reactor path 210 and then to the spectrometer 110.

At the same time, in step 414, the spectrometer 110 collects infrared spectra of the sample matrix since the analyte has been reacted in the reactor 250. The controller then determines the interference spectrum.

In step 416, the controller 105 uses the collected interference spectra to create an interference calibration file. If band-limited analysis is to be used, and where the analyte is EO, then the calibration file covers the spectral range of interest (ie. 2,500-3,500 $cm^{-1}$) with a unit value of 1.00. And, in step 418, the controller 105 automatically adds the interference calibration file to the gas analysis method.

In some cases, the controller averages the interference spectra to reduce noise in a regression analysis. If the interference gases are rapidly changing it may not make sense to co-add or spectrally average these data, however. Thus, the controller 105 can choose not to average or average only if the data are stable. Since spectral non-linearity (rather than detector non-linearity) can be encountered, it is impossible to know in advance if the spectral features will co-add properly since they may be fundamentally different at varying concentrations.

In more detail, in some implementations of steps 416 and 418, the controller 105 measures the spectra of the reacted sample stream in step 414 at the spectrometer's fastest rate (e.g., 1 spectrum per second). Then the controller 105 compares the sample spectra to each other. If they are close enough in concentration, such as within 5% of the ppm methane level or 5% of the % water level, the spectra are co-added. Then, the controller 105 collects further spectra and then again co-adds those to the current average spectra if they are also close enough in concentration. This continues until concentration is different by x % or 60 co-adds are obtained. This averaged interference spectrum is then added to the analysis method in step 418.

In other implementations of steps 416 and 418, the controller 105 measures the interference spectra again at the spectrometer's fastest rate. The first two samples, Sample1, Sample2, are compared against each other. If they are close enough in concentration, then Sample1, Sample2 are co-added. On the other hand, if they are sufficiently different, a parallel co-add is started. Then, spectra of more samples, Sample3, are/is created and compared to those of Sample1 and Sample2. If the spectral features of Sample3 are close to either of the previous spectra (of Sample1 and Sample2), the new spectra are co-added; or if they are sufficiently different, the two new samples furthest apart are added to a third group. This process is repeated for more interference spectra such as 60 sample points. Ultimately, the two averaged data sets furthest apart in concentration or two with most co-adds are added to the method.

Then, in step 420, the controller 105 controls the automated valve system 222 switch to the bypass path 212 to provide the sample gas directly to the spectrometer 110.

Finally, in steps 422 and 424, the controller collects the spectra from the spectrometer 110 and analyzes the spectral data for the analyte employing the interference spectra and the calibration file in order to determine the analyte concentration.

Other gases can be added as well including pure component calibrations present in the interference spectrum to make small improvements in the analysis. This can include pure component water and methane calibration spectra as well as the interference spectra. Component calibrations for ethylene, propylene and propylene oxide, which might also be present, can further be added.

This procedure presents significant advantages over using the interference spectrum as a background since the interference spectrum can then be regressed, and the % of interference can be determined and removed. In more detail, in the typical operation of a FTIR, a background is acquired to remove the instrument response function and produce a zero line or a 100% T line from which to measure the analyte. This could be applied here by having the gas flow through the reactor and using the resulting spectra as the background. Then, the sample gas is flowed through the bypass and the compound of interest is measured. Then, the controller just uses the pure gases, water, methane, ethylene, ethylene oxide, propylene, and propylene oxide spectra to measure the EO. So, the interference gases are only measuring the difference in their concentration from when the background was obtained. This is useful especially when the AutoRef function of the FTIR 110 is employed. It is preferable to put all the compounds in the matrix along with the interference spectrum (which removes most of the spectral features) and can be scaled by the regression analysis. So, if the water concentration was reduced by 1%, the regression would use 0.99× this spectrum, if water were the only component in the interference spectrum.

While this invention has been particularly shown and described with references to preferred embodiments thereof, it will be understood by those skilled in the art that various changes in form and details may be made therein without departing from the scope of the invention.

What is claimed is:

1. A gas analysis system, comprising:
a spectrometer configured to analyze gas;
a reaction device configured to selectively provide a sample stream or a reacted sample stream to the spectrometer, wherein the reacted sample is stream is provided by removing at least an analyte of interest from the sample stream;
a system configured to provide the sample stream by reducing water in the gas upstream of the reaction device, wherein reducing water in the gas includes pressuring and then cooling the gas, and wherein providing the sample stream further comprising reducing a pressure of the gas after reducing water in the gas; and
a controller configured to use the reacted sample stream to create spectra for analyzing the sample stream.

2. A system as claimed in claim 1, wherein the system for providing the sample stream includes a pressurization pump to pressurize the gas.

3. A system as claimed in claim 2, wherein the system for providing the sample stream includes a chiller to cool pressurized gas generated by the pressurization pump.

4. A system as claimed in claim 1, wherein the controller analyzes the sample stream by measuring ethylene oxide in the sample stream.

5. A system as claimed in claim 1, wherein the controller analyzes the sample stream by measuring siloxanes in the sample stream.

6. A system as claimed in claim 1, wherein the reaction device includes an oxidation catalyst.

7. A system as claimed in claim 1, wherein the reaction device includes a furnace reactor.

8. A system as claimed in claim 1, wherein the controller determines when to provide the sample stream and when to provide the reacted sample stream to the spectrometer from the reaction device.

9. A system as claimed in claim 1, wherein the controller determines when to provide the sample stream and when to provide the reacted sample stream to the spectrometer from the reaction device by monitoring a residual spectrum.

10. A system as claimed in claim 1, wherein the reaction device includes a preheater for heating the sample stream before flowing into a reactor.

11. A system as claimed in claim 1, wherein the reaction device includes one selected from a group consisting of a thermal catalytic oxidizer reactor, a UV illumination or photo-ionization reactor, and a chemical reactor with reagent.

12. A system as claimed in claim 1, wherein the spectrometer includes one selected from a group consisting of an infrared absorption spectrometer, a mass spectrometer, an ion mobility spectrometer, a cavity ring down spectrometer, a tunable diode laser, an electrochemical sensor, and a gas chromatograph.

13. A system as claimed in claim 1, wherein the spectrometer is a Fourier transform spectrometer.

14. A gas analysis method, comprising:
analyzing a gas with a spectrometer;
providing a sample stream by reducing water in the gas, wherein reducing water in the gas includes pressuring and then cooling the gas, wherein providing the sample stream further comprises reducing a pressure of the gas after reducing water in the gas;
switching between a sample mode and an interference mode for selectively providing the sample stream or a reacted sample stream to the spectrometer, wherein the reacted sample stream is provided by removing at least an analyte of interest from the sample stream; and using the reacted sample stream to create spectra for analyzing the sample stream.

15. A method as claimed in claim 14, wherein analyzing the sample stream includes measuring ethylene oxide in the sample stream.

16. A method as claimed in claim 14, wherein analyzing the sample stream includes measuring siloxanes in the sample stream.

17. The method of claim 14, wherein pressurizing the gas includes pressuring the gas to over 3 atmospheres.

18. The method of claim 14, wherein reducing the pressure of the gas includes reducing the pressure of the gas to less than 3 atmospheres.

19. The method of claim 14, wherein analyzing the gas with the spectrometer includes measuring spectra of the sample stream or the reacted sample stream at a pressure greater than 1 atmosphere.

20. The method of claim 14, wherein switching between the sample mode and the interference mode is based on monitoring a residual spectrum.

21. The method of claim 14, further comprising preheating the sample stream before flowing the sample stream into a reactor.

* * * * *